United States Patent
Kuslich et al.

[19]

[11] Patent Number: 6,086,589
[45] Date of Patent: Jul. 11, 2000

[54] METHOD AND DEVICE FOR FIXING SPONDYLOLISTHESIS POSTERIORLY

[75] Inventors: Stephen D. Kuslich, Stillwater; James Ahern, Hopkins, both of Minn.

[73] Assignee: Spineology, Inc., Stillwater, Minn.

[21] Appl. No.: 09/241,473

[22] Filed: Feb. 2, 1999

[51] Int. Cl.[7] .................................................. A61B 17/56
[52] U.S. Cl. .............................................................. 606/61
[58] Field of Search ................................. 606/60, 61, 72, 606/73, 62, 64, 65, 67; 623/17

[56] References Cited

U.S. PATENT DOCUMENTS

| | | |
|---|---|---|
| 2,414,882 | 1/1947 | Longfellow . |
| 2,537,070 | 1/1951 | Longfellow . |
| 3,977,398 | 8/1976 | Burstein . |
| 4,653,481 | 3/1987 | Howland et al. . |
| 5,116,336 | 5/1992 | Frigg .......................................... 606/65 |
| 5,531,747 | 7/1996 | Ray . |
| 5,593,409 | 1/1997 | Michelson .................................. 606/61 |
| 5,601,556 | 2/1997 | Pisharodi . |
| 5,669,909 | 9/1997 | Zdeblick et al. ........................... 606/61 |

OTHER PUBLICATIONS

Treatment of Severe Spondylolisthesis with Posterior Interbody Fusion Using Fibular Strut Graft; Authors: Stephen I Esses, M.D., Nazar Natout, M.D., Phelps Kip, M.D.

*Primary Examiner*—Michael Buiz
*Assistant Examiner*—Vy Q Bui
*Attorney, Agent, or Firm*—Vidas, Arrett & Steinkraus, PA

[57] ABSTRACT

A method and apparatus for fixation of spondylolisthesis includes an elongated, threaded, hollow shaft which is threaded into a bore hole correctly formed between correctly aligned vertebrae posteriorly. The shaft includes a plurality of openings therethrough in the distal and proximal ends to allow bone and fibrous through growth to stabilize the vertebrae to decrease associated pain.

4 Claims, 3 Drawing Sheets

METHOD AND DEVICE FOR FIXING SPONDYLOLISTHESIS POSTERIORLY

BACKGROUND OF THE INVENTION

1. Field of the Invention

This invention relates to a method and apparatus for fixing of spondylolisthesis, e.g., misalignment of the vertebrae comprising the spinal column. More specifically, the present invention relates to an apparatus which is screwed into a drill hole through one vertebra into the adjacent vertebra and a method utilizing that apparatus.

2. Description of the Related Art

Treatments for conditions involving subluxation of one vertebrae upon another, resulting in misalignment of the spinal column, involve the use of screws which extend through a plate and which are tightened to draw the misaligned vertebrae back into alignment. U.S. Pat. No. 5,531,747 to Ray (hereinafter "Ray") is an example of a plate and screw system for treating spondylolisthesis. Other approaches include insertion of an implant into the disk space between misaligned vertebrae such as shown in U.S. Pat. No. 5,601,556 to Pisharodi (hereinafter "Pisharodi"). The Ray approach has its limitations as discussed in Pisharodi. That patent has a disadvantage in requiring removal of the disk and having multiple steps, that is, two implants are inserted into the disk space only to be substituted later with monolithic implants. Henry Bohlman has described a fibular strut used to treat spondylolisthesis with a portion of donated fibular bone in "Spondylolisthesis Treated by a Single-Stage Operation Combing Decompression With In Situ Posterolateral and Anterior Fusion", *J. Bone and Joint Surg.*, 72-A: 415–421, March 1990. This involves obtaining a piece of the fibula of a deceased donor, machining it into the size and shape needed and inserting it into a cavity formed to hopefully make a tight fit.

Many examples of fixation of joints have been described in the literature, including U.S. Pat. No. 4,653,481 to Wiltse (hereinafter "Wiltse"). Many of the approaches involve sophisticated, multi-part systems requiring extensive surgery and many sizes of parts to accommodate different sized patients.

There is, therefore, a need for an improved method of treatment of conditions involving misalignment of the vertebrae of the spinal column, or spondylolisthesis, and it is a principal object of the present invention to provide such a method and an apparatus for use in connection with that method.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. § 1.56(a) exists.

SUMMARY OF THE INVENTION

The invention provides an elongated, hollow, threaded shaft that is inserted into a bore hole drilled between adjacent vertebrae to hold the vertebrae in alignment after release of the temporary alignment by surgeons. The shaft includes a plurality of openings through the shaft into its bore to allow in growth material inserted there within to come in contact with bone and the disk. Preferably, the shaft is partially inserted and bone in growth material is injected into the drill hole and disk space prior to fully positioning the shaft.

Once placed, the apparatus provides a fixation of the spondylolisthesis and maintains the alignment by virtue of its design and addition of bone in growth material into the drill hole and disk space.

BRIEF DESCRIPTION OF THE DRAWINGS

A detailed description of the invention is hereafter described with specific reference being made to the drawings in which.

DESCRIPTION OF THE PREFERRED EMBODIMENTS

Figure 1:
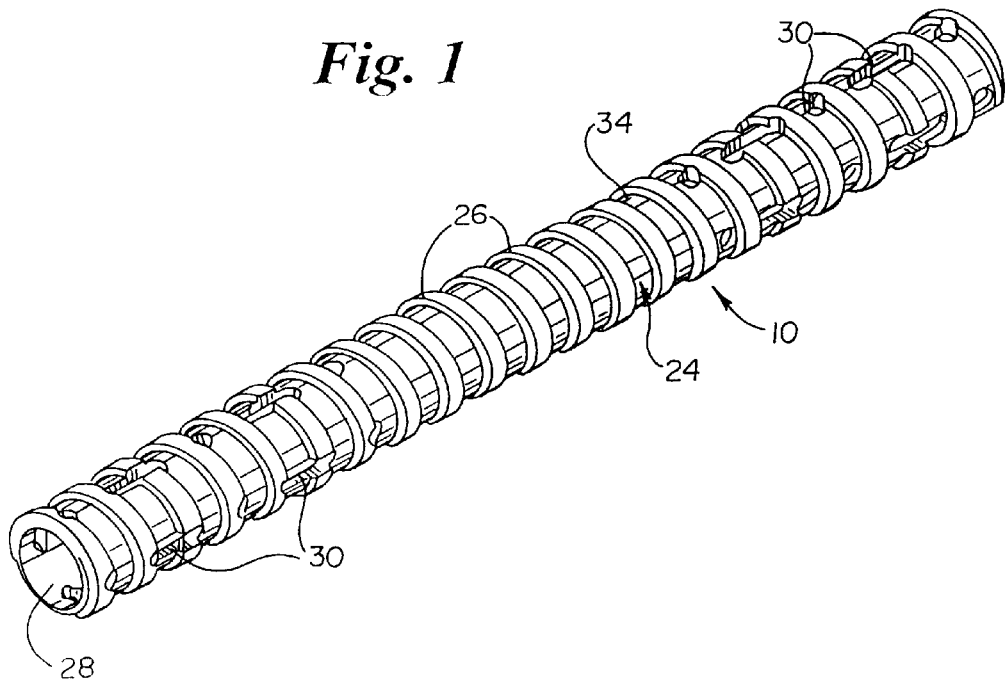
FIG. 1 is a perspective view of the apparatus of the invention.
Figure 2:
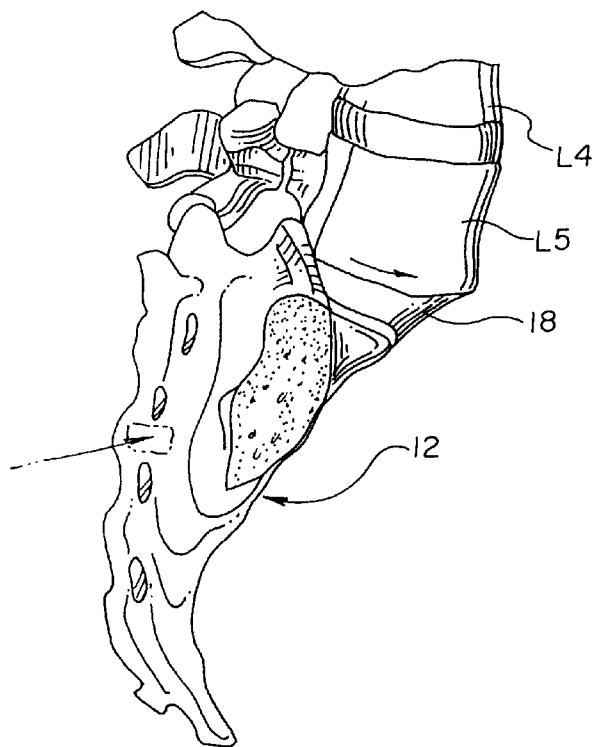
FIG. 2 is a side view of the sacrum and L4 and L5 vertebrae.
Figure 3:
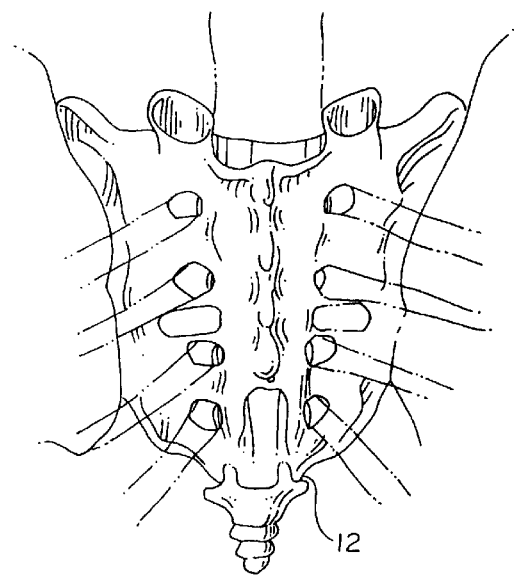
FIG. 3 is a posterior view of the vertebrae of FIG. 2.
Figure 4:
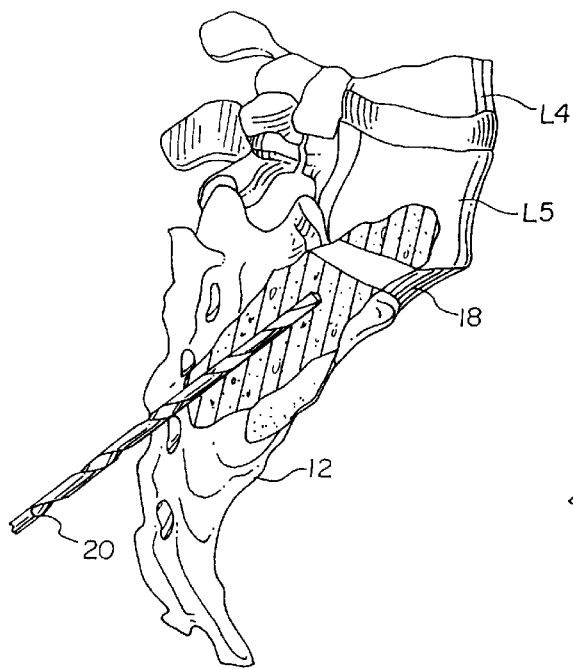
FIG. 4 is a side view of the vertebrae showing a drill hole being formed through the sacrum into the L5 vertebra.

With reference to the Figures, it will be seen that a typical misalignment, or spondylolisthesis of vertebrae occurs in between the sacrum 12 and the L5 and L4 vertebrae. Typically, the L5 vertebra is pushed anteriorly from the desired position. As shown in FIGS. 2 and 4, a drill 20 is positioned and drilled posteriorly from the sacrum through the disk 18 and into the L5 vertebra to form a drill hole 22. This drilling is performed after surgeons temporarily align the sacrum 12 and L5 vertebra, if deemed necessary. If reduction and correction is desired, the alignment is not simply fixed to prevent further pain, but is corrected by changing the alignment. It should be noted that a pair of the devices are typically employed, as best shown in FIG. 3, which show where the drill holes 22 would be directed through the sacrum 12.

As shown in FIGS. 1, 5, 6 and 7, apparatus 10 is essentially a hollow screw having a long shaft 24, a central bore 28, threads 26 and a plurality of through bores or side openings 30 communicating between the interior and exterior of the shaft. The side openings 30 increase the ability of the device to lock firmly into the fixed joint by bone in growth. The central portion 34 has no openings since it will be in the disk space 18 and needs greater strength to cover the gap between the vertebrae until in growth fuses the joint completely.

Figure 5:
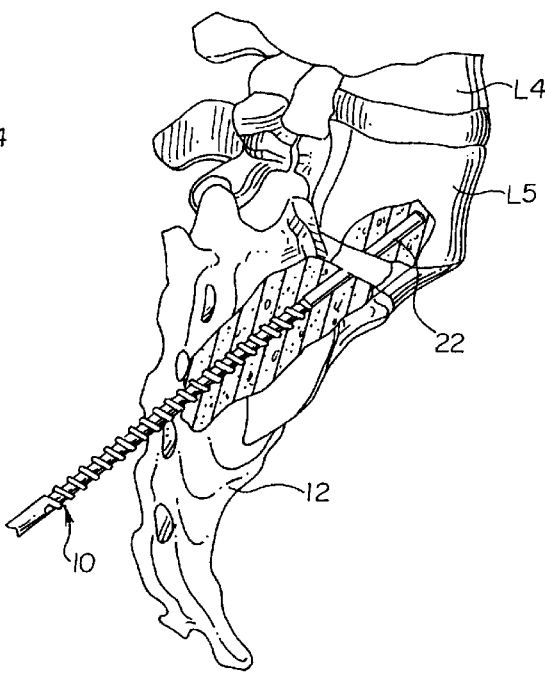
FIG. 5 is a side view showing the apparatus of the invention being threaded into the drill hole of FIG. 4.
Figure 6:
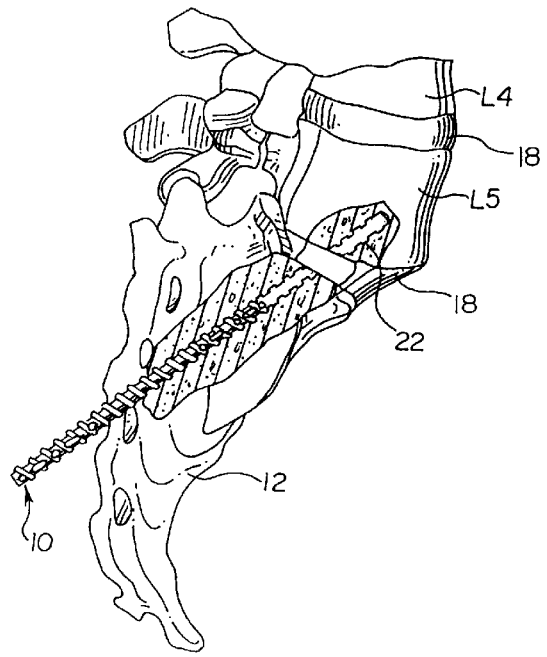
FIG. 6 is a side view showing the apparatus being inserted into a pre-threaded opening.
Figure 7:
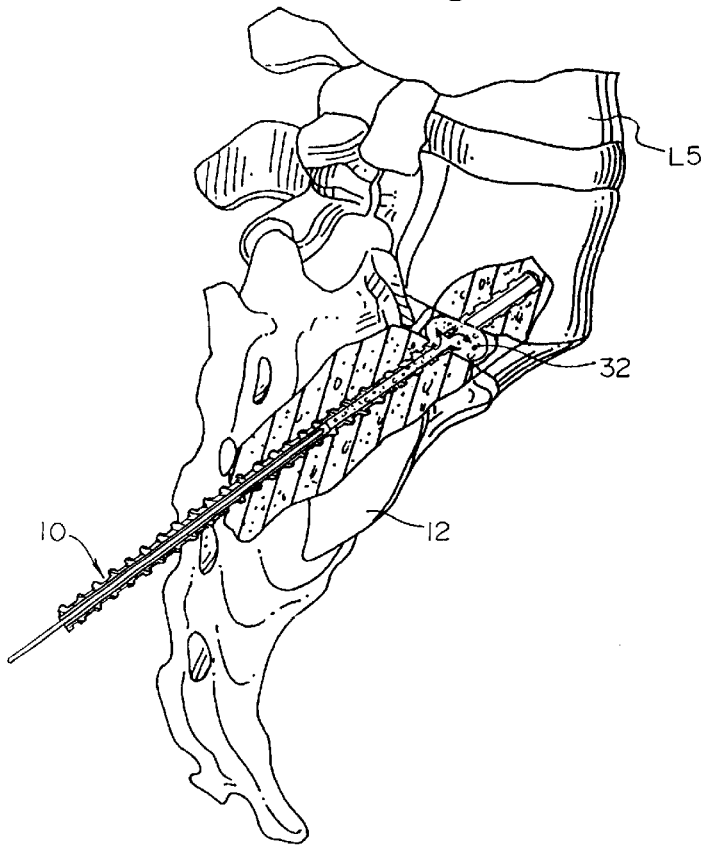
FIG. 7 is a side view showing insertion of bone in growth material into the bore of the apparatus and into the disk space.

The disk 18 is typically reamed out with conventional techniques. The interdiscal space thus formed is preferably filled with a bone in growth media 32 such as morselized bone chips, hydroxylapatite, bone morphogenic protein (BMP) or any of the acceptable bone in growth media that fosters a bony union across adjacent vertebrae. The apparatus 10 is threaded into drill hole 22 as shown in FIG. 5. The apparatus 10 is then inserted fully allowing the apparatus 10 to keep the sacrum 12 and L5 vertebra in alignment and stabilize the joint. Any temporary re-alignment made by the surgeons may be released, as the apparatus 10 now holds the load. The bone in growth material 32 is free to cause a bony or fibrous union through the apparatus openings 30 and in the disk space 10 to increase the stabilization of the area. The drill hole 22 may be tapped to include threads matching those of the apparatus 10 or the apparatus threads 26 may be self-tapping. As shown in the Figures, the bone in growth material 32 may be inserted through the bore 28 of device 10, although the size of the bone in growth particles may require introduction before the device is inserted. Alternatively, the bone in growth material 32 may be inserted through the side of the disk 18 into the interdiscal space.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. Apparatus for aligning adjacent vertebrae comprising:

an elongated, hollow shaft having a distal and a proximal end and a central portion, said shaft having a length sufficient to pass through one vertebra, through an interdiscal space and substantially into an adjacent vertebra, said shaft defining a cylinder, said shaft including a through bore between the ends and an exterior and an interior surface, said exterior surface including bone engaging members to increase bone-holding, said shaft further including a plurality of openings between the exterior and the interior surfaces of the shaft to allow passage of bone in growth material therethrough; said plurality of openings being formed adjacent the proximal and distal ends with no openings in the central portion for the length of the vertebral disk.

2. The apparatus of claim 1 wherein said bone engaging members are external threads.

3. A method for posteriorly correcting spondylolisthesis comprising the steps of:

(a) temporarily aligning adjacent vertebrae in need of realignment;

(b) drilling a drill hole posteriorly through one said vertebra into the other said vertebra through a disk therebetween;

(c) inserting bone in growth material into the drill hole through said disk;

(d) inserting a threaded, elongated hollow screw into said drill hole through one said vertebra, through said disk and into said other vertebra; and (e) removing said temporary alignment.

4. A method for posteriorly fixing spondylolisthesis comprising the steps of:

(a) drilling a drill hole posteriorly through a vertebra in need of fixation to another vertebra through a disk therebetween;

(b) reaming out the disk to create an interdiscal space;

(c) inserting bone in growth material into the interdiscal space; and (d) inserting a threaded, elongated hollow screw into said drill hole through one said vertebra, through said disk and into said other vertebra.

* * * * *

UNITED STATES PATENT AND TRADEMARK OFFICE
CERTIFICATE OF CORRECTION

PATENT NO. : 6,086,589

DATED : July 11, 2000

INVENTOR(S) : Stephen D. Kuslich, James Ahern

It is certified that error appears in the above-identified patent and that said Letters Patent is hereby corrected as shown below:

Column 1, line 63: delete "in growth", insert -- ingrowth --
Column 1, line 63: delete "there within", insert -- therewithin --
Column 1, line 65: delete "in growth", insert -- ingrowth --
Column 2, line 3: delete "in growth", insert --- ingrowth --
Column 2, line 23: delete "in growth", insert -- ingrowth --
Column 2, line 49-50: delete "in growth", insert -- ingrowth --
Column 2, line 52: delete "in growth", insert -- ingrowth --
Column 2, line 58: delete "in growth", insert -- ingrowth --
Column 2, line 65: delete "in growth", insert -- ingrowth --
Column 3, line 5: delete "in growth", insert -- ingrowth --
Column 3, line 7: delete "in growth", insert -- ingrowth --
Column 3, line 34: delete "in growth", insert -- ingrowth --
Column 4, line 14: delete "in growth", insert -- ingrowth --
Colum 4, line 27: delete "in growth", insert -- ingrowth --

Signed and Sealed this

Fifteenth Day of May, 2001

Attest:

NICHOLAS P. GODICI

*Attesting Officer*  *Acting Director of the United States Patent and Trademark Office*